(12) United States Patent
Pulavskyi (10) Patent No.: US 10,531,836 B2
(45) Date of Patent: Jan. 14, 2020

(54) DEVICE, AND SYSTEM FOR SIGNAL DECOMPOSITION, TRACKING, ANALYSIS, AND RECONSTRUCTION

(71) Applicant: INTERNATIONAL TECHNOLOGY CENTER FZC, Ras Al Khaimah (AE)

(72) Inventor: Anatolii Pulavskyi, Kharkov (UA)

(73) Assignee: INTERNATIONAL TECHNOLOGY CENTER FZC, Ras Al Khamiah (AE)

( * ) Notice: Subject to any disclaimer, the term of this patent is extended or adjusted under 35 U.S.C. 154(b) by 513 days.

(21) Appl. No.: 15/049,099

(22) Filed: Feb. 21, 2016

(65) Prior Publication Data

US 2017/0238880 A1 Aug. 24, 2017

(51) Int. Cl.
*A61B 5/00* (2006.01)
*H04L 29/08* (2006.01)
*A61B 5/0245* (2006.01)
*A61B 5/145* (2006.01)

(52) U.S. Cl.
CPC .......... *A61B 5/7275* (2013.01); *A61B 5/0006* (2013.01); *A61B 5/0245* (2013.01); *A61B 5/14532* (2013.01); *A61B 5/726* (2013.01); *A61B 5/7246* (2013.01); *A61B 5/7278* (2013.01); *A61B 5/7282* (2013.01); *H04L 67/1097* (2013.01)

(58) Field of Classification Search
USPC .................................................. 600/509–510
See application file for complete search history.

(56) References Cited

U.S. PATENT DOCUMENTS

2015/0272500 A1* 10/2015 Kan-tor ................ A61B 5/7267
600/301

* cited by examiner

*Primary Examiner* — Nicole F Lavert
*Assistant Examiner* — Nicole F Johnson
(74) *Attorney, Agent, or Firm* — Inventa Capital PLC

(57) ABSTRACT

A system and method for representing quasi-periodic electrocardiography waveforms, wherein system employs a hybrid-coding scheme combining linear predictive coding techniques based upon Algebraic Code Excited Linear Prediction with a discrete wavelet transforms.

6 Claims, 5 Drawing Sheets

DEVICE, AND SYSTEM FOR SIGNAL DECOMPOSITION, TRACKING, ANALYSIS, AND RECONSTRUCTION

FIELD OF THE INVENTION

This invention relates to the field of computer-implemented systems and methods, and more specifically a software, embedded-circuits or firmware implemented system and method to decompose signals in a data structures to store such signals having quasi-periodic wave properties.

BACKGROUND OF THE INVENTION

The digital representation of waveforms is a technology that is central to various sectors of industry where the detection of periodic and non-periodic waveforms can be critical to determining whether an erratic heartbeat, electrical short circuit, or some other problem exists. A digital representation must clearly and accurately represent the analog source of a waveform, but at the same time be able to accomplish such things as, compressing the incoming data into some manageable size, and maintain the integrity of the incoming data (i.e., making sure that the digital representation has enough fidelity to the original signal to be useful). Of additional import is the ability to have a digital representation that can consistently allow one to identify the presence and location of certain wave features, and/or that lends itself to certain types of automated analyses.

High-fidelity digital representations are problematic for a number of reasons. First, they require relatively large amounts of space within which to store the digitized data. Put another way, the higher the fidelity of the digitized data, the larger the amount of storage needed. Another problem with high-fidelity digital representations is that they can result in large amounts of digital data that has little or no import in terms of conveying meaning. For example, a periodic wave signal that merely repeats the same waveform does not convey much meaning to the person analyzing the waveform, and may in fact just take up storage space with unremarkable data. An additional problem is the repeated sampling, over sampling of such high-fidelity data even though it is otherwise unremarkable. Such over sampling results in wasted processing bandwidth (i.e., processor cycles, and/or power) as well as data bandwidth (data storage space and/or transmission bandwidth).

U.S. Pat. No. 8,086,304 issued on Dec. 27, 2011, with the title "Physiologic signal processing to determine a cardiac condition" describes, that in a method for determining a cardiac condition, a sensed physiologic signal for a period including multiple cardiac cycles is received. A plurality of harmonics of the received physiologic signal is extracted based on a reference frequency, wherein the harmonics correspond to a plurality of alternant frequencies. Amplitudes of at least some of the extracted harmonics are determined, and are used to determine an alternant indicator value.

U.S. Pat. No. 9,209,782 describes a system and method for represented quasi-periodic waveforms comprising, representing a plurality of limited decompositions of the quasi-periodic waveform, wherein each decomposition includes a first and second amplitude value and at least one time value.

What is needed is a method and structure that efficiently and accurately captures the underlying waveform, with little or no degradation of the value and meaning of that waveform data. In particular, what is needed is a method and apparatus that tracks and records the properties of a particular frequency component of a complex waveform.

SUMMARY OF THE INVENTION

In some embodiments, the present invention provides a method and apparatus that tracks and records a particular frequency component (e.g., the rate and amplitude of the lowest frequency of, for example, a heartbeat of an electrocardiogram (ECG) signal) as that frequency component changes frequency over a wide range of frequencies.

In some embodiments, the present invention provides a method and apparatus that tracks and records the properties of a particular frequency component, such as the component corresponding to the time-local fundamental period of a quasi-periodic waveform as that frequency component varies in frequency over a wide range of frequencies.

For example, the rate and amplitude of the frequency component corresponding to, for example, the local cardiac cycle length of an electrocardiogram (ECG) signal, or a seismic signal.

Some embodiments provide a method and apparatus that perform digital filtering using a plurality of banks of filters whose frequency ranges overlap and whose center frequencies are closely spaced and performing wavelet transforms on frequency components.

Then tracking the components with the strongest signal within one of the overlapping filter banks. Such that a particular frequency component that changes frequency over time can be tracked as its frequency shifts to higher or lower frequencies. In order to track that component as its frequency or period changes over a large range.

In some embodiments, changes in frequency of up to 2:1 or 3:1 or more can be tracked. For example, a human heartbeat can often vary from fifty beats per minute (50 BPM, or even as low as 30 BPM or less) to two-hundred beats per minute (200 BPM or even 300 BPM or more). In some embodiments, the present invention tracks a component of the cardiac signal over a range of about thirty beats per minute or less to three-hundred beats per minute or more (a range of 5:1). In some embodiments, the present invention tracks each of a plurality of frequency components of such a varying heartbeat, wherein each of the components shifts in frequency as the BPM rate changes.

In some embodiments, the present invention includes a system and method for representing quasi-periodic waveforms. For example, in some embodiments, the detailed mapping from input blocks of ECG samples in 16 bit uniform PCM format to encoded blocks of bits and from encoded blocks of bits to output blocks of reconstructed ECG samples is explained.

The procedure of this invention is intended for implementation in all network entities and User Equipment (UE)s supporting the present invention. A system and method for representing quasi-periodic electrocardiography waveforms, wherein system employs a hybrid-coding scheme combining linear predictive coding techniques based upon Algebraic Code Excited Linear Prediction (ACELP), predominantly for cardiac signals, with a discrete wavelet transforms and a transform coding method, for generic content. The decoder generates the signal parameters represented by the indices transmitted in the bit-stream.

Accordingly, one aspect of the present invention provides a method and system that tracks and records a particular frequency component (e.g., the rate and amplitude of the lowest (i.e., fundamental) frequency of, for example, the cardiac cycle of an electrocardiogram (ECG) signal) as that frequency component changes frequency over a wide range of frequencies.

For a fuller understanding of the nature and advantage of the present invention, reference should be made to the ensuing detailed description and accompanying drawing. Other aspects, objects, and advantages of the invention will be apparent from the drawings and detailed description that follows.

BRIEF DESCRIPTION OF THE DRAWINGS

The invention will be more readily understood from the following description of embodiments thereof given, by way of example only, with reference to the accompanying drawings, in which.

DETAILED DESCRIPTION OF THE INVENTION

Although the following detailed description contains many specifics for the purpose of illustration, a person of ordinary skill in the art will appreciate that many variations and alterations to the following details are within the scope of the invention.

Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention.

Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

Regarding the reference numbers appearing in the Figures—the same reference number is used throughout when referring to an identical component that appears in multiple Figures. The same reference number or label may refer to signals and connections, and the actual meaning will be clear from its use in the context of the description.

To solve this problem the method used discrete wavelet transform. The standard electrocardiogram was used as a basic signal to be recorded during the research. The ECG sampling rate was 2000 Hz; the dynamic range of the analog-to-digital converter was 12 bits.

Linear Prediction & ECG

Observable Data Sequence is Random Vector $$X^m = (X_0, X_1, \ldots, X_{m-1})^t$$

Optimal 1-Step Linear Prediction is the Optimal Linear Predictor $$\bar{X}_m = (a_{m-1}, \ldots, a_2, a_1)^t X^m.$$

Efficient inversion to find $a_m$ is Levinson-Durbin algorithm. How apply linear prediction to produce low bit rate ECG of sufficient quality for ECG understanding and decease recognition? E.g., reproducing waveform (waveform coding) or use model to synthesize (ECG coding). Wide literature exists on all of these topics in a speech context and they are intimately related. (See, e.g., John Makhoul, "Linear prediction: a tutorial review," Proceedings of the IEEE, Vol. 63, No. 4, April 1975 and J. D. Markel and A. H. Gray Jr's classic book Linear Prediction of Speech, Springer-Verlag, 1976.

Discrete Wavelet Transform

The following method is proposed quantization coefficients $a_m$ of linear prediction. The basis is taken fast Haar wavelet transform for the sequence order of m=16. This conversion is carried out in four stages.

Figure 1:
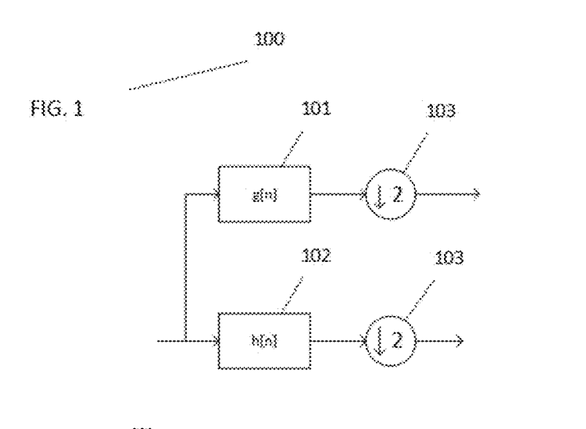
FIG. 1 is a block diagram of filter analysis 100 and one level of the transform.

FIG. 1 is a block diagram of filter analysis 100 and one level of the transform. The discrete wavelet transform (DWT) of a signal $a_m$ is calculated by passing it through a series of filters. First, the samples are passed through a low pass filter 101 with impulse response g[n].

The signal is also decomposed simultaneously using a high-pass filter 102 h[n]. The outputs giving the detail coefficients (from the high-pass filter) and approximation coefficients (from the low-pass). It is important that the two filters are related to each other and they are known as a quadrature mirror filter.

However, since half the frequencies of the signal have now been removed, half the samples can be discarded according to Nyquist's rule. Decimators 103 are then sub-sampled the filter outputs by two.

This decomposition has halved the time resolution since only half of each filter output characterizes the signal. However, each output has half the frequency band of the input so the frequency resolution has been doubled.

The Lifting scheme is an optimization where these two computations are interleaved.

Cascading and Filter banks. This decomposition is repeated to further increase the frequency resolution and the approximation coefficients decomposed with high and low pass filters and then down-sampled. This is represented as a binary tree with nodes representing a sub-space with a different time-frequency localization.

Figure 2:
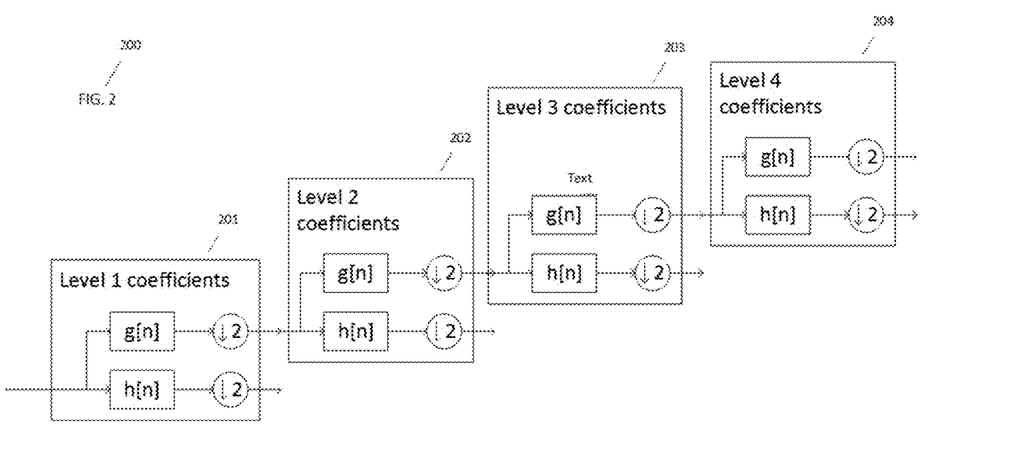
FIG. 2 is a block diagram of four level filter bank.

FIG. 2 is a block diagram of four level filter bank. At each level in the above diagram, the signal is decomposed into low and high frequencies. Due to the process of decomposition, the input signal must be a multiple of 2n where n is the number of levels.

The 2×2 Haar matrix that is associated with the Haar wavelet is H2. Using the discrete wavelet transform, one can transform any sequence of even length into a sequence of two-component-vectors. If one right-multiplies each vector with the matrix H2, one gets the result of one stage 201 of the fast Haar-wavelet transform. Usually one separates the sequences g[n] and h[n] and continues with transforming the sequence g[n]. Sequence g[n] is often referred to as the averages part, whereas h[n] is known as the details part (see Ruch, David K.; Van Fleet, Patrick J. (2009). Wavelet Theory: An Elementary Approach with Applications. John Wiley & Sons). If one has a sequence of length a multiple of four, one can build blocks of four elements and transform them in a similar manner with the 4×4 Haar matrix, which combines two stages 202 of the fast Haar-wavelet transform. Three stages 203 have the 8×8 Haar matrix, four stages 204 have the 16×16 Haar matrix.

The Computation of Line Spectral Frequencies

Let us consider the first level of this scheme that form approximation and detail coefficients.

The coefficients $a_m$ are converted to the LSP representation (see IEEE Transactions on Acoustic, Speech and Signals Processing, Vol. 2, April, pp. 9-12 (1993): "Immittance spectral pairs (ISP) for speech encoding", Bistritz, Y., and Peller, S.) for quantization and interpolation purposes.

The low pass filter for the discrete Haar wavelet transform has impulse response $$g[n]=[1,1].$$

The coefficients of first polynomial are found by the following recursive relations for i=1, . . . , 8:

$$f_1(i)=a_i+a_{16-i}f_1(i-1), \text{ where } f_1(0)=0$$

The high pass decomposition filter for the discrete Haar wavelet transform has impulse response $$h[n]=[-1,1].$$

The coefficients of second polynomial are found by the following recursive relations for i=1, . . . , 8:

$$f_2(i)=a_i-a_{16-i}+f_2(i-1), \text{ where } f_2(0)=0$$

The both polynomials are symmetric and asymmetric, respectively. It can be proved that all roots of these polynomials lie on the unit circle and are interlaced. The first and second polynomials have each 8 conjugate roots, called the Line Spectral Pairs (LSPs) and denoted $$\cos(\omega_i)=q_i.$$

The corresponding angular frequencies are the Line Spectral Frequencies (LSFs). The LSFs satisfy the ordering property $$0<\omega_0<\omega_{15}<\pi.$$

Considering the Frequency Mapping $$\cos(\omega)=x$$

we can define $$T_m(x)=\cos(m\omega)$$

$a_n$ mth-order Chebyshev polynomial in x.
The Chebyshev polynomials satisfy the order recursion $$b_k(x)=2\times b_{k+1}(x)+b_{k+2}(x)+f_k(x)$$

with initial conditions $$b_8(x)=b_9(x)=0.$$

This recursion can be used to calculate the line spectral frequencies using this sigma notation where, k represents the index of summation; 0 is the lower bound of summation, and 7 is the upper bound of summation $$2\Sigma[b_k(x)+2\times b_{k+1}(x)+b_{k+2}(x)]T_k(x)=f_0(x)+b_0(x)+b_2(x).$$

The details about Chebyshev polynomial evaluation method can be found in IEEE Transactions on Acoustic, Speech and Signals Processing, Vol. 34, No. 6, December, pp. 1419-1426 (1986): "The computation of line spectral frequencies using Chebyshev polynomials", Kabal, P., and Ramachandran, R. P.

This decomposition is repeated to further decrease the predictor order from 16 through 2. In case of a four level filter bank the predictor order takes the four values: 16, 8, 4, 2.

Processing of ECG Signal

Figure 3:
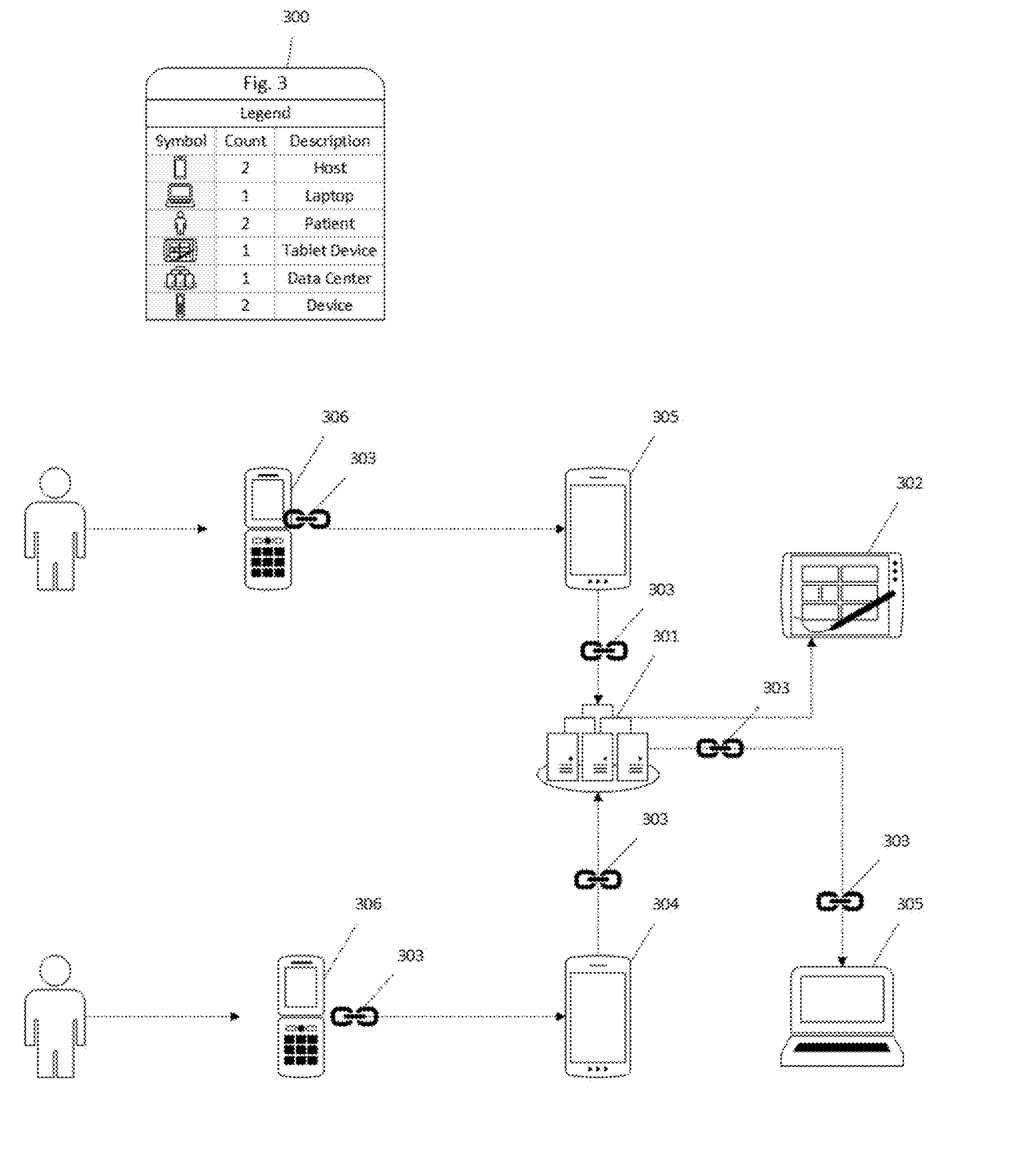
FIG. 3 is a block diagram of a system 300 wherein data related to quasi-periodic waveforms (Data) is stored in a database of data center 301.

FIG. 3 is a block diagram of a system 300 wherein data related to quasi-periodic waveforms (Data) is stored in a data base of data center 301. This data center as input for a computer program utilizing the above-described method, data structure, and/or program contained on a tablet device 302, and executed by a central processing unit. In some embodiments, input to execute the program can come by way of a laptop 303. In still other embodiments, input to execute the program can come by way of a peripheral device such as a mouse, light pen, touch screen, touchpad, or any other input device known in the art. In some embodiments, another program to execute and process wave data can call the described method. Once processed, data processed sing the above-described method, data structure, and/or program can be outputted to a display of tablet device 302, or sent via a communicate link 303 to another patient's Host 304 (one example of which is discussed further in the below-described FIG. 5). In some embodiments, the output can be placed into a laptop database 305 or another database located off-site. The Host 304 are connected to a sensing device 306 (one example of which is discussed further in the below-described FIG. 4).

Figure 4:
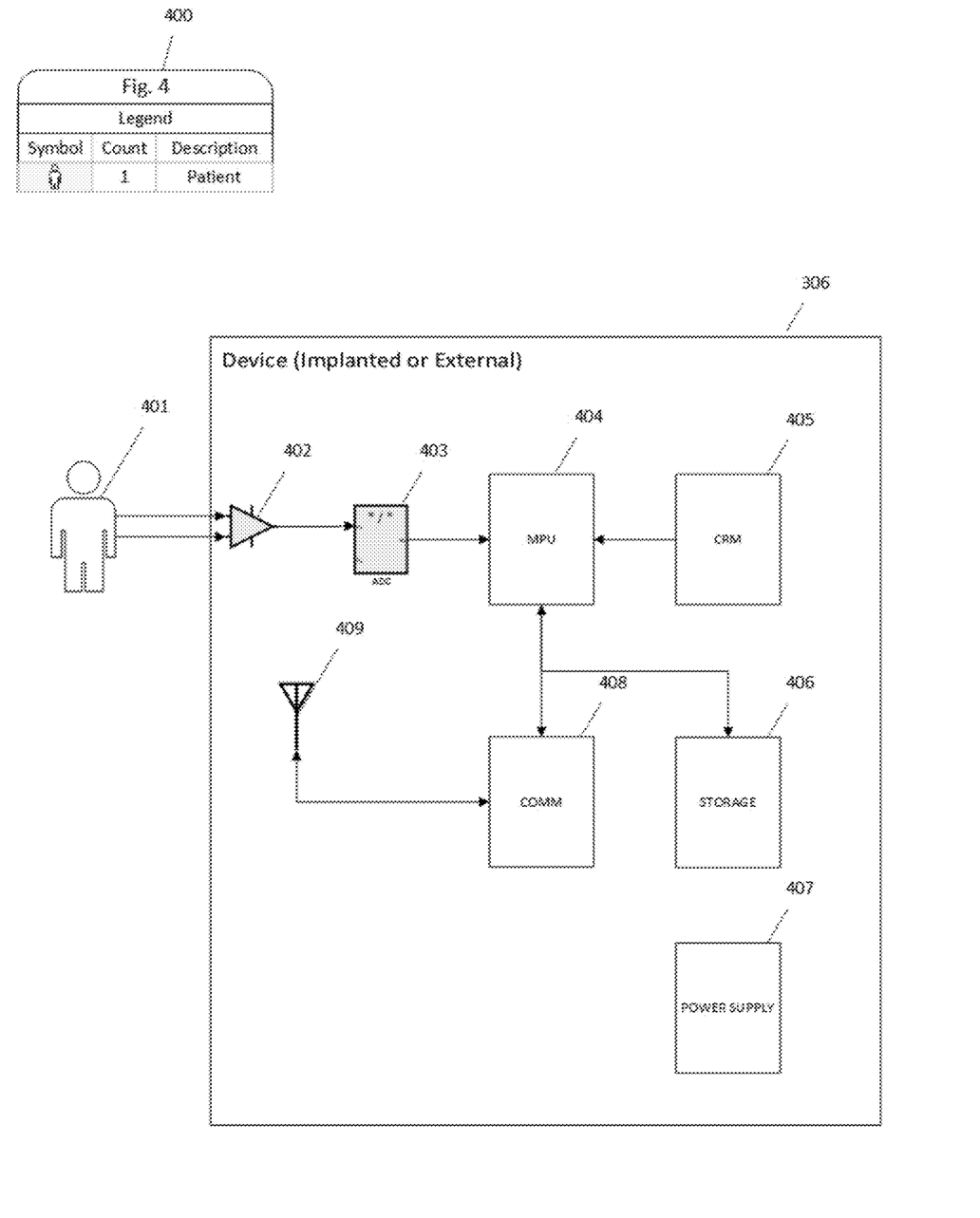
FIG. 4 is a block diagram of a system 400 wherein the original wave signal is an ECG from a patient 401 and including an ECG signal collection and processing device 306.

FIG. 4 is a block diagram of a system 400 wherein the original wave signal is an ECG. In this system, a set of electrodes 401 (leads) is disposed around, on, or within a human body in a manner to produce a desired differential voltage across them representing the voltage gradient generated by the electrical properties of the cardiac tissue. One or more electrodes 401 may be disposed on the skin surface of the body, underneath the skin surface (i.e., a subcutaneous application), and/or additionally, within the heart (i.e., an intra cardiac application). Two electrical poles 402 (poles) are formed by tying together two disjoint sets, each of one or more such disposed electrodes 401. The term vector is used in this context interchangeably for the directed voltage gradient and/or the simple voltage difference across the poles. The term leads is used interchangeably with the poles and/or the leads from which they are constructed, but generally implies a construction of one or more poles from the set of individual leads.

The leads 401 are connected to a sensing device 306 (Device) which is either implanted into the human body or resides external to the human body. The Device 306 in this example contains a set of units or modules, including a difference-amplifier module, an analog-to-digital converter 403 (ADC), a microprocessor unit 404 (MPU), associated computer-readable medium (CRM) 405 containing program instructions, memory storage 406 (Storage), and a power source for supplying power 407 (Power Supply) to the contained modules. The Device may also contain a communications module 408 (COMM) and an associated communications link 409. This communication module and link, in some embodiments, may have a wireless means of providing ECG data.

The differential voltage existing across the leads is measured and/or sensed by presenting the leads to a difference amplifier 402. In some embodiments, the difference amplifier is presumed to contain analog filtering sufficient to substantially meet predetermined requirements for signal-to-noise ratio (SNR) optimization and/or anti-aliasing. In this example, the output of the difference amplifier is digitized using an ADC 403. The output samples from the ADC 403 may then be used as the original signal for this invention example. This original signal is passed to the MPU 404 for processing.

Multiple sensing vectors may be accommodated with multiple lead arrangements, as is well understood and established in the art. (See An Introduction to Electrocardiography 7th Edition, by Leo Schamroth, Blackwell Scientific, 1990.) In this case, each differential lead pair could connect to its own processing chain and can be defined here to include a difference amplifier followed by an ADC 403, producing a corresponding original signal for each sensing vector so processed. Each resulting original signal would then be passed to the MPU 404 for processing.

The MPU 404 executes software and/or firmware stored on computer-readable medium 405 to perform the various tasks necessary for basic function of the Device, and/or to generally fulfill feature and functionality requirements of the Device. The storage of data values representing the original signal and/or the associated objects can, in some embodiments, be in the storage 406 or the computer-readable medium 405.

Figure 5:
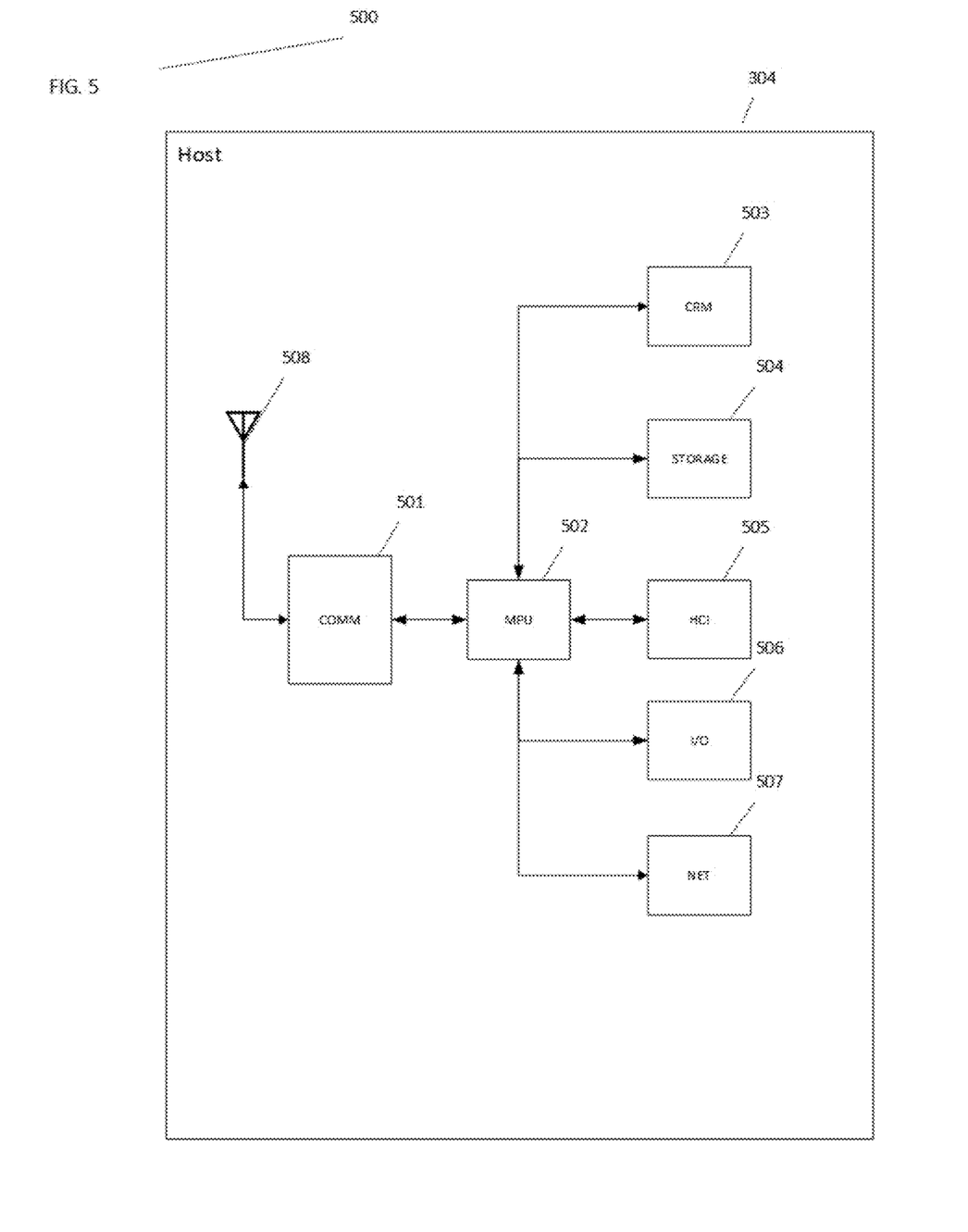
FIG. 5 is a block diagram of a system 500 that depicts a host 304.

In some embodiments, the communications module 408 is used to send outgoing transmissions from the Device 306 to a Host 304 for further processing, evaluation, storage and/or transmission to other similar or different Hosts on a network. The communications module 408 is also used to receive incoming transmissions from a Host 304 which may to be the same as or distinct from the Host 304 used for outgoing transmissions. In some embodiments, incoming transmissions may include commands, data, and/or firmware/software updates as necessary to perform the basic function of the Device 306, and/or to generally fulfill feature requirements of the Device 306. For an implanted Device 306, the connection between the communications module 408 and a Host 304 would be typically implemented in wireless fashion, using methods including but not limited to magnetic, capacitive, and/or RF, all well understood and established in the art. (See Principles of Wireless Networks: A Unified Approach 1st Edition, by Kaveh Pahlavan, Prashant Krishnamurthy, Prentice Hall, 2001.) For an external Device, the connection may be wireless or wired using methods also well understood and established in the art.

FIG. 5 is a block diagram of a system 500 that depicts a Host 304. In some embodiments, it may include a set of units or modules. A communications module 501 (Comm) and associated communications link 508 mean for communicating with the Device 306. A microprocessor unit 502 (MPU) includes a computer-readable medium 503 containing a set of application instructions, an associated storage module 504 (Storage) containing data values representing the original signal. A Human-Computer Interface 505 (HCI) by which an operator (e.g., a physician, technician, or patient) may interact with the MPU 502 and which may include a visual display, auditory display, keyboard, touch screen, haptic device, or other means of interaction. Also described is an Input/output module 506 (I/O) for generally connecting to, and communicating with, computer peripherals such as for example printers, scanners, and/or data acquisition or imaging equipment, and a network communications module 507 (Net) for communicating with other hosts on a computer network such as Ethernet and/or a wireless network, or WiFi. A Power Supply unit is not drawn for the Host, as such a unit may exist entirely within any or all of the individual modules, and so is assumed to exist in the host system as needed.

Figure 6:
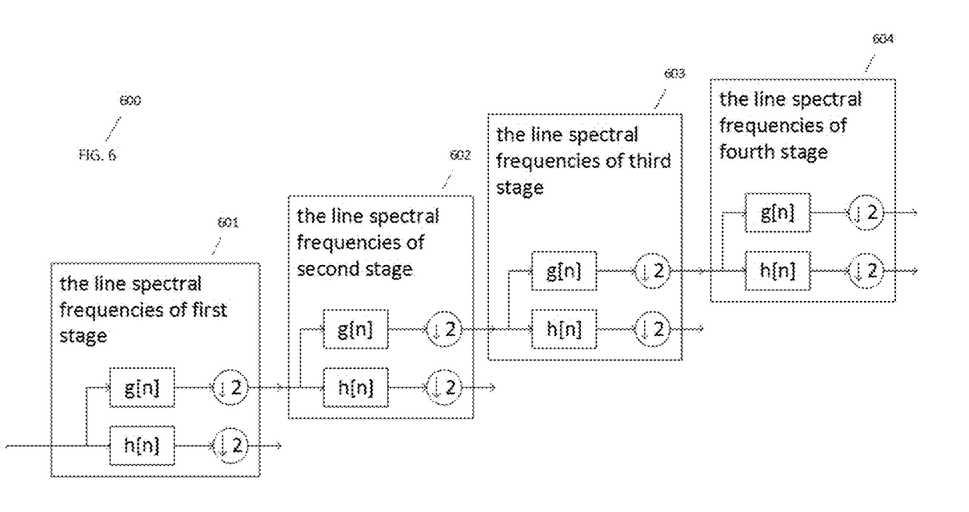
FIG. 6 is a block diagram of a system 600 that depicts an interpretive process executed with device 306 and data center 301.

FIG. 6 is a block diagram of a system 600 that depicts how line spectral frequencies computes using discrete wavelet transform for electrocardiograms processing. In some embodiments, by arranging at least four of the plurality of data structures into line spectral frequencies of first stage 601 from level 1 coefficients; line spectral frequencies of second stage 602 from level 2 coefficients; line spectral frequencies of third stage 603 from level 3 coefficients; line spectral frequencies of fourth stage 604 from level 4 coefficients.

In some embodiments, the proposed method evaluates the clinical and biochemical indicators in blood of a mammal, especially a human. For two years, we've been examining a few groups of people (the total number of 484 people, men and women) to assess the number of blood parameters using the proposed method, namely: Complete Blood Count, Aspartate transaminase, Alanine transaminase, Total protein, Albumin, Globulin, HbA1C, Urea, Creatinine, Triglycerides, Glucose, Cholesterol, Low-density lipoprotein, High-density lipoprotein, Potassium, Sodium, Calcium, Chlorine. The number of indicators can be increased with the accumulation of experimental data. As a particular example below shows the detailed procedure of testing of the method to assess the blood glucose concentration of patients with type 2 diabetes. Additionally, experimentally it has been achieved high sensitivity and specificity to determine by means of this method, hemoglobin, blood pressure, lipoproteins and cholesterol, ion exchange performance (potassium, sodium, and calcium), triglycerides.

EXAMPLE

In some embodiments, the 50/60 Hz component (power net frequency) was removed from the electrocardiogram before its processing; moreover, the band pass filter of 0.5 . . . 40 Hz was used for the removal of trend and muscle tremor. ECG recording time was 2.5 hours, and the entire signal was divided into 5-minute segments. A sixteenth order linear prediction filter was used as a main signal processing procedure. Thus, a vector of 16 parameters was formed for each ECG.

The research was conducted on male volunteers suffering from type 2 diabetes. Number of volunteers: 75. Patients suffering serious heart muscle disorders were not involved. The standard oral glucose tolerance test was used as a basis. Research duration was 2.5 hours and included several stages. The research was conducted in the morning on an empty stomach. For this purpose, an examined volunteer was motionless and laid on his/her back during this research period. No manipulations were conducted with the patient within first 30 minutes. 30 minutes later, venous blood samples were taken from the patient, and thereafter-oral administration of D-glucose dissolved in 75 g of water was proposed. Thereafter, the venous blood sampling was being performed every 15 minutes within two hours to determine the concentration of glucose (total nine venous blood samplings within the research period were conducted). ECGs have been recorded in 12 standard leads throughout the whole research period. ECG records of I-lead (left hand, right hand) have been analyzed. The first lead was chosen intentionally: this is the only lead that can be comfortably used for independent personal use. After the research, three ECG records have been formed. The first 5-minute ECG have been recorded 10-minutes prior to glucose administration.

The second 5-minute ECG has been recorded 5 minutes prior to glucose administration. The third one have been selected from the two-hour ECG at the moment when the concentration of glucose reached its maximum and exceeded the initial value of blood glucose concentration twofold or more (this initial value should be less than 8 mmol/l before glucose administration). It was assumed that the first and the second ECG records correspond to approximately the same value of blood glucose concentration (less than 8 mmol/l). So the first ECG record was considered as a calibration one, the second ECG was considered as a negative one (i.e. ECG with no changes related to changes in glucose concentration), and the third ECG was considered as a positive one (i.e. ECG with changes related to changes in glucose concentration). 56 patients of 75 patients have met the conditions of compliance of the concentrations mentioned above. Further comparison has been conducted with respect to the calibration record. Thus, the result of correlation of the negative ECG and the ECG and the calibration ECG and the result of correlation of the positive ECG and the calibration ECG has been compared. Standard values in 10-dimensional space has been compared with the thresholds respectively for pairs of vectors of parameters of the regression model: the negative-calibration ECG and the positive-calibration ECG.

In some embodiments, device 306 performs no signal analysis processes except for the process of Storage/Transmission. The original signal samples are merely passed to the communications module 408 of the Device, either directly or perhaps via the MPU 404, perhaps with some formatting of the data for optimal transmission. The Host 304 then performs some or all of the remainder of the signal-analysis processes.

In some embodiments, device 306 performs the Input analysis and the Storage/Transmission Processes, and the Host 304 performs some or all of the remainder of the processes. In the case that the component signals and/or the original signal are not transmitted to the Host 304, they may be estimated on the Data Center 301 end from the transmitted objects via the Host 304.

In some embodiments, the signal-analysis processes are performed, in whole or in part, by execution of software or firmware on the MPU 404 and/or on the MPU 502, using a program stored in the appropriate respective computer-readable medium 503 and/or storage unit 504. Such processing may also be performed, in whole or in part, in dedicated hardware which in this example resides entirely within the MPU 404 and/or on the MPU 502, for example in the form of microcode, in the form of a coprocessor, and/or in the form of peripheral hardware.

As used herein, a quasi-periodic waveform is a signal that may be considered as the linear combination of a series of locally periodic component signals, each having different periods and/or shapes, with locality exhibited on the order of a cycle to a few cycles. Examples of quasi-periodic waveforms that can be processed and analyzed by the present invention include but are not limited to:

general biological signals from humans or animals such as ECG waveforms, intracardiac electrogram (EGM) waveforms, EEG waveforms, EMG waveforms, EOG waveforms, blood pressure waveforms, plethysmography waveforms, heart sounds, ultrasound signals, MRI signals, bio-impedance waveforms, electro-dermal testing and polygraph signals;

natural phenomena such as solar sunspot cycles, climate patterns, patterns of El NiZo, drought cycles, seismic activity (i.e., earthquakes in certain areas occur approximately every N years, and major earthquakes can be preceded by relatively minor seismic activity that exhibit quasi-periodic characteristics), ocean currents and tides, and occurrence of tsunamis;

manufacturing process signals for feedback and control;

demographics and societal patterns such as population cycles, product market preferences, crowd noise, traffic patterns, traffic noise, and industrial noise;

vehicular signals pertaining to feedback, control, and detection and diagnosis of issues associated with operation and/or service of a vehicle, such as engine and transmission noise, temperature, information from any number of different types of sensors such as oxygen sensors, temperature sensors, pressure sensors, and flow sensors;

aircraft performance-related signals, such as from laminar flow sensors, pressure sensors, wind shear sensors and down-draft sensors;

financial time series, representing for example prices of stocks, equities, securities, commodities, bonds, mutual funds, and futures, and economic cycles including micro and macro-economic phenomena;

content-carrying signals, such as music, speech or video signals (including analysis and compression of such signals);

telemetry signals for applications such as radar (including, for example, Synthetic Aperture Radar (SAR), Terrain Following Radar (TFR), and Forward-Looking Infrared (FUR) radar) and sonar;

communications signals such as transmitted over an optical fiber, cable or remote radio link (including spread-spectrum transmissions), such as weak signals from satellites and spacecraft or animal-tracking devices, cordless and cellular telephones, and wireless computer networks such as those using the IEEE802.11 standard;

analysis of data storage medium signals such as from a magnetic disk head or a laser optical receiver for optical storage media; and other signals exhibiting quasi-periodic behavior, including seismic signals obtained for oil exploration.

Other embodiments involving various permutations and distributions of processes or blocks within the Device and Host are specifically contemplated to fall within the scope of this current invention. Some embodiments include combinations or subcombinations of a plurality of items listed individually or within one or more groups of other items.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

I claim:

1. A non-invasive device for monitoring physiological conditions, the device comprising:
   a set of electrodes (leads) is disposed around, on, or within a human body in a manner to produce a desired differential voltage across them representing the voltage gradient generated by the electrical properties of the cardiac tissue; and
   a sensing device connected to the set of electrodes which is either implanted into the human body or resides external to the human body, that comprising a microprocessor unit which determines whether to activate an alarm that the monitored person's health is at risk;
   wherein microprocessor unit performing a linear prediction (LP) analysis on the digitized signal to obtain the coefficients of the synthesis filter of the CELP model for the digitalized signal using the autocorrelation approach, the autocorrelation of windowed quasi-periodic waveform is converted to the LP coefficients using the Levinson-Durbin algorithm;
   wherein the LP coefficients of the synthesis filter through a Haar discreet wavelet transformation is converted to the Line Spectral Frequencies (LSFs) form data associated with shot-term prediction and excitation; and
   wherein microprocessor unit reduces the size of the information containing in the plurality of data structures based on Chebyshev polynomial evaluation method.

2. The device of claim 1, wherein the n-level filter bank gets the LP coefficients decomposed into low and high frequencies, due to the process of decomposition, the number of the LP coefficients must be a multiple of 2n where n is the number of levels.

3. The device of claim 1, wherein the microprocessor unit executes a classification algorithm in order to determine evaluates the clinical and biochemical indicators in blood of a mammal, especially a human.

4. A non-invasive system for monitoring physiological conditions, the system comprising:
   the device of claim 1;
   wherein the microprocessor unit is not mounted to the sensing device.

5. The system of claim 4, wherein data related to quasi-periodic waveforms (Data) are stored in a data base of data center, this data center as input for a computer program utilizing the above-described method, data structure, and/or program contained on a tablet device, and executed by a central processing unit.

6. The system of claim 4, wherein a Human-Computer Interface (HCI) by which an operator (e.g., a physician, technician, or patient) may interact with the MPU and which may include a visual display, auditory display, keyboard, touch screen, haptic device, or other means of interaction.

* * * * *